United States Patent [19]

Cohen et al.

[11] Patent Number: 4,986,256

[45] Date of Patent: Jan. 22, 1991

[54] USE OF PARAMAGNETIC METALLOPORPHYRINS AS CONTRAST AGENTS FOR TUMORS IN MRI IMAGING

[75] Inventors: Jack S. Cohen, Bethesda; Chi-Wan Chen, Silver Spring; Charles E. Myers, Rockville, all of Md.; Miriam Sohn, Washington, D.C.

[73] Assignee: The United States of America as represented by the Department of Health and Human Services, Washington, D.C.

[21] Appl. No.: 706,622

[22] Filed: Feb. 28, 1985
(Under 37 CFR 1.47)

[51] Int. Cl.$^5$ .............................................. A61B 17/52
[52] U.S. Cl. ................................ 128/653.4; 128/654; 424/9
[58] Field of Search .................. 128/1.1, 1.3, 653, 654; 424/1.1, 9

[56] References Cited

U.S. PATENT DOCUMENTS

| | | |
|---|---|---|
| 4,136,683 | 1/1979 | Gordon . |
| 4,266,549 | 5/1981 | Kimura . |
| 4,298,590 | 11/1981 | Bogoch . |
| 4,354,499 | 10/1982 | Damadian . |
| 4,386,087 | 5/1983 | LaVallee .............................. 514/185 |
| 4,393,071 | 7/1983 | Fujii et al. . |
| 4,411,270 | 10/1983 | Damadian . |

FOREIGN PATENT DOCUMENTS

| | | |
|---|---|---|
| 0071564 | 2/1983 | European Pat. Off. . |
| 0133603 | 2/1985 | European Pat. Off. . |
| 2109407 | 6/1983 | United Kingdom ................ 436/548 |

OTHER PUBLICATIONS

Zanelli et al., *Synthetic Porphyrins as Tumor-Localizing Agents* in Br. Journal of Radiology, vol. 54, 1981, pp. 403-407.

Winkelman et al., The Concentration in Tumor and Other Tissues of Parenterally Administered Tritium and $^{14}$C-Labeled Tetraphenyl porphinesulfonate in Cancer Research, vol. 27, Nov. 1967, pp. 2060-2064.

Chi-Wan Chen et al., "Paramagnetic Metalloporphy-rins as Potential Contrast Agents in NMR Imaging", Mar. 1984-NIH, vol. 168, No. 1.

"Society of Magnetic Resonance in Medicine"-Program and Book of Abstracts-Third Annual Meeting, 8/13-17, 1984, New York, N.Y.

Theodore S. T. Wang et al.,-"Metalloporphyrin Derivatives:Structure-Localization Properties", 1980.

"Scientific Paper Application"-70th Assembly of the Radiological Society of North America.

"1984 Abstract Form for Scientific Papers and Posters-Society of Magnetic Resonance in Medicine-3rd Annual Meeting, New York, N.Y".

"NMR-Imaging of Brain Tumours With Gadolinium-DTPA in Humans".

"Porphyrin Products"-a Catalog Describing Various Commercially Available Porphyrin Derivatives.

"Bioinorganic Chemistry 5,87-92(1975)"-The Distribution of Various Water Soluble Radioactive Metalloporphyrins in Tumor Bearing Mice.

"Metalloporphyrin Contrast Agents for Magnetic Resonance-Imaging of Human Tumors in Mice"-N. J. Patronas et al.

R. H. Knop et al.,-"Contrast Enhancement of Experimental Tumors in Magnetic Resonance"-3rd Conf. on Mag. Res. in Medicine, N.Y., Aug. 13-17, 1984.

Weinmann et al.-"A Contrast Medium for Magnetic Resonance Imaging"-Publication date unknown.

1984-Scientific Paper Application-70th Scientific Assembly of the Radiological Society of North America.

(List continued on next page.)

Primary Examiner—Stephen C. Pellegrino
Assistant Examiner—Mark F. Colosimo
Attorney, Agent, or Firm—Browdy and Neimark

[57] ABSTRACT

Water-soluble paramagnetic metalloporphyrins are used as contrast enhancing agents for magnetic resonance imaging. These agents exhibit excellent localization, non-toxicity and suprisingly high contrast enhancement in magnetic resonance imaging applications.

4 Claims, 2 Drawing Sheets

OTHER PUBLICATIONS

Robert C. Brasch, M.D.-"Work in Progress: Methods of Contrast Enhancement for NMR Imaging and Potential Applications".

Commentary-"Porphyrin Localization: A New Modality for Detection and Therapy of Tumors".

James A. Nelson, M.D.-Porphyrin Chelates of Paramagnetic Metals (et al).

Leon S. Jackson et al.-Manganese Protoporphyrin IX: "A Potential Intravenous Paramagnetic NMR Contrast Agent".

Duane D. Blatter, M.D. et al.-Manganese Protoporphyrin IX and Manganese Uroporphyrin:-"Tissue Selective Magnetic Resonance Contrast Agents".

USE OF PARAMAGNETIC METALLOPORPHYRINS AS CONTRAST AGENTS FOR TUMORS IN MRI IMAGING

BACKGROUND OF THE INVENTION

This invention relates generally to magnetic resonance imagining (MRI) and more particularly to MRI using ligands as contrast agents.

For several years, magnetic resonance imaging (MRI) has been proposed as a valuable aid in diagnosing and locating malignant tumors. It has, for example, been known that certain paramagnetic metal ions localize in malignant tumors and decrease the relaxation time ($T_1$) of hydrogen ions present in water there. Nevertheless, the use of metal ions as contrast agents has been hampered by their inherent high toxicity.

Recently, it has been found that porphyrin and many of its derivatives also localize in malignant tumors. Unfortunately, free porphyrins do not sufficiently effect the relaxation time of water to be effective MRI contrast agents.

Metalloporphyrins have, to some extent, been used to achieve higher contrast on X-rays of neoplastic tissue. One difficulty observed with the use of metalloporphyrins in this context has been the tendancy of some metalloporphyrins to dissociate and release the highly toxic metal ion. Additionally, it is noted that the characteristics of a suitable X-ray image enhancer and a suitable magnetic resonance image enhancer are quite different.

As stated in Brasch, *Radiology*, Vol. 147, No. 3 (1983), pages 781–788, incorporated herein by reference the criteria for the "ideal" contrast enhancer are as follows:

1. The effects of the contrast agent on the NMR signal should be dependent on concentration and should be reproducible from one examination to the next.
2. The agent should be chemically versatile so that it can be bound to other compounds as a biologic probe and thereby permit selective tissue targeting.
3. The substance should have relatively strong NMR activity (paramagnetism) so as to significantly alter local magnetic characteristics in low concentrations.
4. The contrast agent should be chemically stable and easily stored, preferably in a form suitable for immediate administration.
5. The substance should be relatively easily manufactured from inexpensive starting materials.
6. The substance should be non-reactive in vivo and should be nontoxic in diagnostic doses. Toxicity includes mutagenicity, teratogenicity, carcinogenicity, and immunogenicity.
7. The ideal NMR agent should be quickly deactivated or excreted (i.e., within hours).

Thus, it is not always possible to accurately predict the behavior of a particular potential contrast enhancer, especially when in vivo use is considered. For example, in vivo, there is typically competition from naturally occuring biological compounds for water. This competition reduces the available protons upon which the metalloporphyrin can act to enhance proton spin relaxation and therefore increase signal intensity.

SUMMARY OF THE INVENTION

Figure 1:
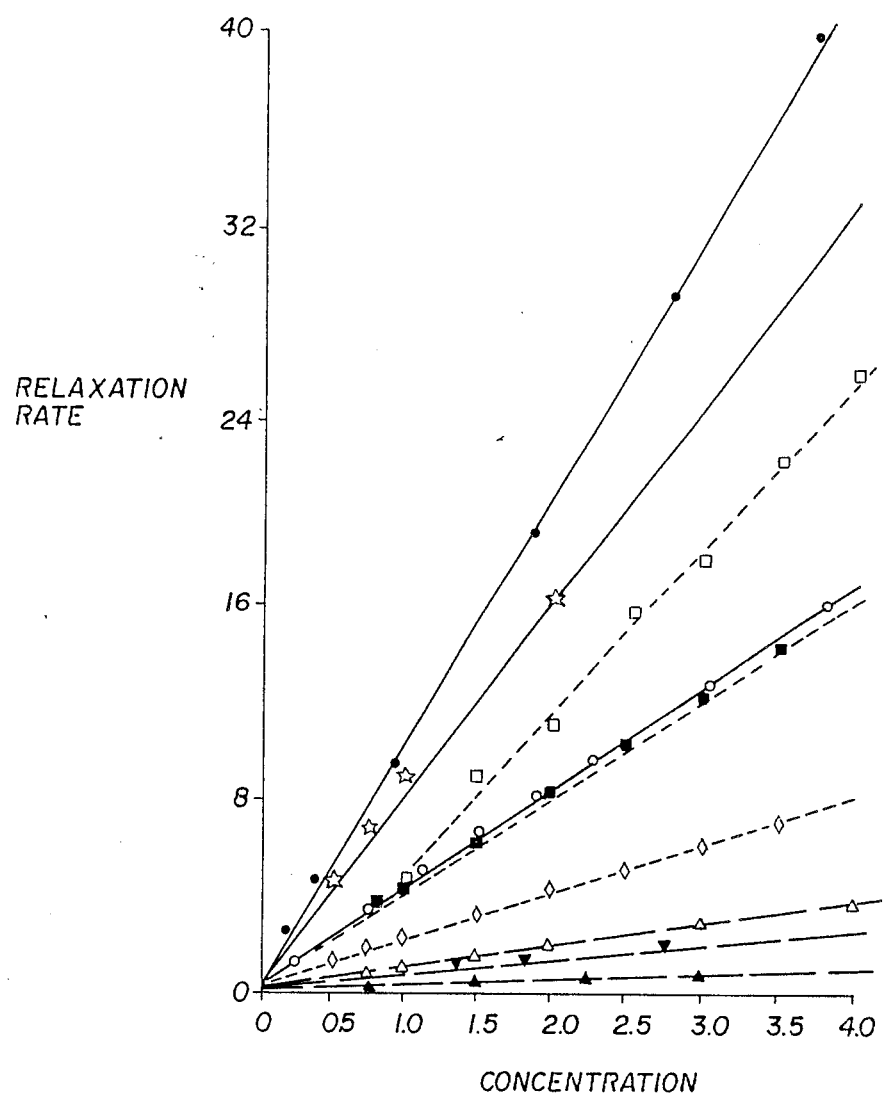
FIG. 1 Spin lattice relaxation rate ($1/T_1$) of water as a function of concentration of metal ion or metallo-TTPS$_4$ complex. Lines are least-square fits: (—) Mn, (---)Fe,(---) Cu. Symbols are for experimental data: (●) Mn(III)TTPS$_4$, (○) Mn(OAc)$_3$, (*) MnCl$_2$, (■) Fe(III)TPPS$_4$, (□) FeCl$_3$, (◊) FeEDTA, (▲) Cu(II)TTPS$_4$, (△) CuCl$_2$ or CuSO$_4$, (▼) Cu(II)TPPS$_4$—CH$_3$.

It is an object of this invention to provide a method for enhancing contrast in MRI images.

It is another object of this invention to provide a method for enhanced magnetic resonance imaging in malignant tumors.

It is a further object of this invention to provide a method for enhancing the contrast in MRI images of malignant tumors by the administration of a relatively safe contrast enhancing compound which decreases the $T_1$, of water and preferentially localizes in malignant tumors.

These and other objects are achieved by the injection of a water soluble paramagnetic metalloporphyrin into a subject prior to obtaining a magnetic resonance image of the subject. Almost any pharmaceutically acceptable water soluble metalloporphyrin should be useful in the process of the present invention. Several known porphyrins are structurally illustrated in Hambright et al, *Bioinorganic Chemistry* 5, 87–92 (1975), incorporated herein by reference as well as in Kessel, *Biochemical Pharmacology*, Vol. 33, No. 9, 1389–1393 (1984), incorporated herein by reference. The structural nature of the binding between the metal and the porphyrin is shown below under the heading "Description of the Preferred Embodiment". The structural nature of this binding does not differ significantly across various metalloporphyrins shown there. Manganese-porphyrins are especially preferred.

DETAILED DESCRIPTION OF THE PREFERRED EMBODIMENT

Generally, the degree of image enhancement a paramagnetic metal-containing contrast enhancer provides is directly proportional to the magnetic moment of the metal ion and the number of unpaired electrons in the metal ion. Thus, Mn (II) and Fe (III), each with 5 unpaired electrons have been considered to have the largest degree of image enhancement among transition elements. Ions with fewer unpaired electrons have been considered to have less of an enhancement effect.

Most metalloporphyrins exhibit far less contrast enhancement activity than their corresponding salts. For example, Fe(III) Cl$_3$ a slope for $1/T_1,=6.82\pm0.20$(mM•s)$^{-1}$, while Fe(III)-3 tetrasulphonated tetraphenylporphyrin Fe(III)TPPS$^4$) had a slope for $1/T_1,=3.91\pm0.02$ (mM•s)$^{-1}$. Cu(II) TPPS$_4$ has an expectedly smaller effect on $T_1$, having a slope for $1/T_1=0.139\pm0.004$ (mM•s)$^{-1}$.

Since Mn(II)Cl$_2$ has exhibited a greater slope for $1/T_1$ ($8.03\pm0.12$(mM•s)$^{-1}$) than the corresponding Fe(III) salt, it had been hoped that complexes of Mn(II) with porphyrins would be better image enhancers than Fe(III) complexes. Nevertheless, Mn(II) Mn(III) complexes with several known porphyrins readily dissociate. Mn(III) has only 4 unpaired electrons and its salt has a lesser slope for $1/T_1$ ($4.04\pm0.01$ (mM•s)$^{-1}$ than the corresponding Mn(II) salt. Thus, the improved results over Fe(III) TPPS$_4$ that were obtained using a Mn(III)-porphyrin were unexpected.

EXPERIMENT 1

Materials

Reagent grade $CuCl_2 \cdot 2H_2O$ (Fisher), $CuSO_4 \cdot 5H_2O$ (Allied), $FeCl_3 \cdot 6H_2O$ (Baker), $MnCl_2 \cdot 4H_2O$ (Baker), and FeEDTA (EDTA, ferric-sodium salt with 1.5 equiv. $H_2O$; Sigma) were used without further purification. Practical grade $Mn(OAc)_3 \cdot H_2O$(Fluka) was purified by filtration to remove some insoluble material. Cu(II)TPPS$_4$ (sodium salt, $C_{44}H_{24}N_4CuO_{12}Na_4S_4 \cdot 4HOAc \cdot H_2O$ [III]), Fe(III)TPPS$_4$ (acid form, $C_{44}H_{28}N_4\text{-}FeO_{12}S_4 \cdot Cl \cdot 2H_2O$ [IV]), and Mn(III)TPPS$_4$ (acid form, $C_{44}H_{28}N_4MnO_{12}S_4 \cdot Cl \cdot 4H_2O$[V]) were purchased from Porphyrin Products, Logan, UT. Cu(II)TPPS$_4$—CH$_3$ (sodium salt, $C_{45}H_{27}CuN_4O_{12}Na_4S_4 \cdot CF_3SO_3 \cdot 5H_2O$ [VI]) was supplied by the Drug Synthesis and Chemistry Branch, NCI. Pyridine impurities were removed by treatment with a suitable acid such as HCl. All metalloporphyrins were analyzed for C, H, Cl (when applicable), N, S, and the relevant metal, and were found to have chemical compositions consistent with these molecular formulae and solvents of crystallization. The oxidation state of the manganese in Mn(III)TPPS$_4$ was determined from its characteristic UV absorption in water by comparison with the spectrum of the corresponding Mn(II)TPPS$_4$, which was obtained by sodium hydrosulfide reduction of Mn(III)TPPS$_4$ in a sealed container. The absorption maxima for the Mn(III) derivative were 465, 561 and 593 nm, while those for the Mn(II) derivative were 434, 572, and 612 nm.

Methods

All $T_1$ and $T_2$ measurements were performed on an IBM PC-20 series NMR Analyzer (Minispec) at 20 MHz, with a 13 mm probe, and a microprocessor which provides automatic calculation of $T_1$ or $T_2$ (in s). All measurements were carried out at 37° C., determined with a copper-constantan thermocouple in a glass sleeve inserted into the sample tube prior to the measurement. The maximum temperature deviation measured was 0.4° C. after 3–4 min., the time required for the longest experiment. A standard 10 mm round-bottomed NMR tube was placed inside a 13 mm flat-bottomed tube to reduce the sample volume to 2.0–2.2 ml. Aliquots of concentrated solutions were added stepwise to the sample tube to obtain the concentration of metalloporphyrin desired. In general, the $T_1$ data were reproducible in duplicate runs to within 1%, and were consistent with the values calculated in a different computer using the same intensity data and a standard equation of the form, $\ln I(\tau) = A + B(\tau/T_1)$, where I is the intensity, $\tau$ the delay time between the two pulses, and A and B are constants.

TABLE 1

The effect of metallo-TPPS$_4$ complexes on water relaxation rate $(1/T_1)^a$

| Metal ion or complex | Slope $(mM \cdot s)^{-1}$ |
|---|---|
| Mn(III)TPPS$_4$ | 10.36 ± 0.09 |
| Mn(OAc)$_3$ | 4.04 ± 0.01 |
| MnCl$_2$ | 8.03 ± 0.12 |
| Fe(III)TPPS$_4$ | 3.91 ± 0.02 |
| FeCl$_3$[b] | 6.82 ± 0.20 |
| FeEDTA | 1.87 ± 0.01 |
| Cu(II)TPPS$_4$ | 0.139 ± 0.004 |
| Cu(II)TPPS$_4$CH$_3$ | 0.538 ± 0.006 |
| CuCl$_2$ or CuSO$_4$ | 0.836 ± 0.004 |

[a]Data from FIG. 1; (1/T$_1$) intercepts were from 0.26–0.51, while the value for deionized water at 37° C. was 0.26 s$^{-1}$
[b]The linear fit applies only when concentration is higher than 1.0 mM

Results

Four different paramagnetic metallo-TPPS$_4$ complexes were evaluated for their effect on the spin lattice relaxation rate $(1/T_1)$ of water (FIG. 1). The corresponding metal ions (as chloride, sulfate or acetate salts) were also tested for comparison. The results are presented in FIG. 1. The water relaxation rate increases linearly with concentration for all compounds studied (except for FeCl$_3$ below 1 mM). This was expected since it is known that the water relaxation rate is proportional to the concentrations of paramagnetic ions present in solution, according to the equation, $$(1/T_1) = 12\pi\gamma^2\eta\mu^2 N/5kT$$

where T is the gyromagnetic ratio of protons, $\eta$ the solvent viscosity, $\mu$ the effective magnetic moment of the paramagnetic agent, k Boltzmann's constant, T the absolute temperature, and N the number of paramagnetic ions per unit volume. The slopes obtained by linear least-square fitting are given in table 1. The paramagnetic effect falls off rapidly with distance, i.e., $(1/T_1)$ is inversely proportional to $1/r^6$, where r is the mean distance from the paramagnetic center to the water protons. Thus, an effective paramagnetic contrast agent should have a metal ion in a high-spin state (large magnetic moment) and have facile access to coordination sites by water molecules.

Among the 4 metallo-TPPS$_4$ complexes investigated Mn(III)TPPS$_4$ had the greatest effect, increasing the water relaxation rate with a slope of $10.4(mM \cdot s)^{-1}$, and Cu(II)TPPS$_4$ had the smallest effect with a slope of $0.14 (mM \cdot s)^{-1}$. This large difference can be attributed to the fact that Mn(III) has 4 unpaired electron spins, while Cu(II) has only one unpaired spin, and Cu(II) porphyrins do not readily coordinate axial ligands. Cu(II)TPPS$_4$—CH$_3$, an N-methyl-substituted derivative, was more effective (slope $0.54 (mM \cdot s)^{-1}$) than the non-methylated material in increasing the water relaxation rate, apparently due to its non-planar geometry affecting the electronic structure allowing binding of axial water ligands to the metal site. Although Fe(III)TPPS$_4$ with 5 unpaired electron spins was less effective (slope $3.9 (mM \cdot s)^{-1}$) than Mn(III)TPPS$_4$, it was more than twice as e-fective in increasing the water relaxation rate than FeEDTA (slope $1.9 (mM \cdot s)^{-1}$), which has been tested as a potential contrast agent in NMR imaging of rabbits. This clearly shows the advantages, in terms of relative efficacy, of paramagnetic agents having relatively labile axial ligands such as water in metalloporphyrins compared to the EDTA chelating functional groups. Both Cu(II)-and Fe(III)TPPS$_4$ were less effective than their corresponding free metal ions in increasing the water relaxation rate. By contrast, Mn(III)TPPS$_4$ had a greater effect than its corresponding free metal salt. It should be noted that free Mn(III) salts are relatively unstable in solution.

However, Mn(III)TPPS4 is completely stable while Mn(II)TPPS4 is readily oxidized. Mn(III)TPPS4 also had a greater effect than Mn(II)Cl2, which has 5 unpaired electron spins. These differences probably depend upon the rate and the extent of ligand water exchange, and on the degree of delocalization of the unpaired electron spin in the porphyrin ring system.

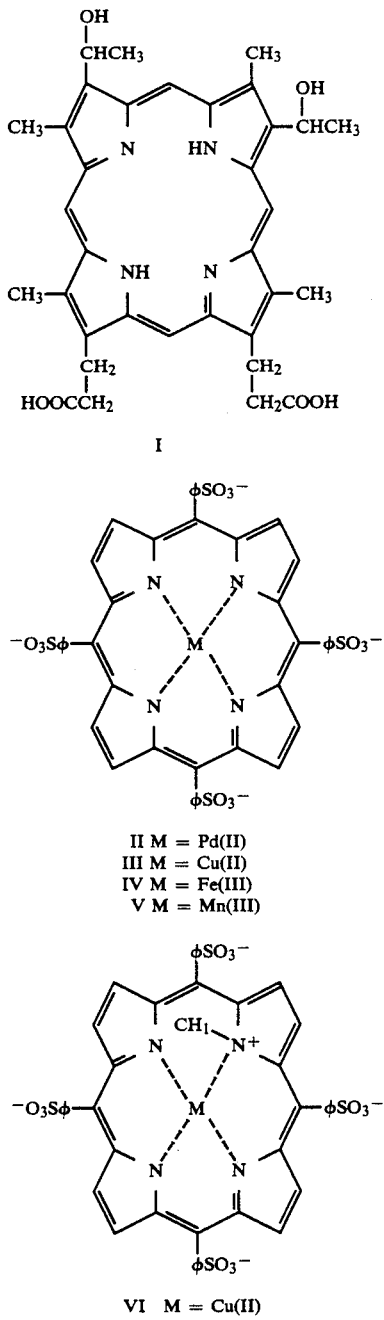

II M = Pd(II)
III M = Cu(II)
IV M = Fe(III)
V M = Mn(III)

VI M = Cu(II)

To test for the effect of another ligand upon the water relaxation rates we carried out parallel experiments adding Mn(III)TPPS4 and Fe(III)TPPS4 to a solution of 0.2M pyridine in water. The slopes of plots of $(1/T_1)$ vs concentration of complex obtained in these experiments were 7.6 and 0.2 (mM• s)$^{-1}$, respectively. In other words, the effectiveness of the Fe(III) complex is reduced by a factor of 20 while that of the Mn(III) complex is only reduced by about 25% by competition of pyridine for water. It has also been shown that the presence of pyridine in water significantly reduces the proportion of the high-spin form of Fe(III)-protoporphyrin. A similar phenomenon may explain the dramatic reduction in the water relaxation rate due to Fe(III)TPPS4 in the presence of pyridine.

The $T_2$ relaxation time of aqueous Mn(III)TPPS4 was also measured as a function of concentration. It was found that the $T_2$ relaxation rate of water also increased linearly with concentration with a slope of 12.6 (mM• s)$^{-1}$. In view of the shorter values of $T_2$ and the consequent greater scatter in the data, these values were not determined in the other cases.

From the above results it is apparent that several of the soluble metalloporphyrins, notably Mn(III)TPPS4, showed great potential as contrast agents in NMR imaging. However, aqueous solution is not the same as the mileau of the cell, and the relative differences in the amount of free water and in the intrinsic relaxation times of water in given tissues, will affect the efficacy of these agents in vivo. In addition, potential coordinating ligands other than water may also significantly reduce their effectiveness in vivo. This may not be a disadvantage since there may be different compartments with different coordinating ligands in different tissues such that the effectiveness of the paramagnetic contrast agents may vary although their concentrations may be the same. These considerations are in addition to the degree of selectivity of retention of metalloporphyrins in different tissues, notably cancerous tissue. By contrast, the order of magnitude of the effect of radiopharmaceuticals is solely dependent on their degree of localization, and not on the coordination chemistry of the metal.

EXPERIMENT 2

Relaxation times ($T_1$ and $T_2$) of bulk water were measured at 20 MHz with an IBM PC20 pulse spectrometer. All measurements were performed at a temperature of 37° C., determined with a glass-encased thermocouple immersed in the sample. The effectiveness of different metalloporphyrins in altering the relaxation rate ($1/T_1$) of water was compared on a molar basis.

The bulk water relaxation times of samples of excised tissues and whole tumors from athymic mice (musmusculus) were measured in the same way, both before and several hours after intravenous infusion with the metalloporphyrins. The solutions used were approximately 10 mg in 0.1 ml of isotonic saline. The mice had implanted human colon carcinoma (S-174T) cells, which has produced malignancies of approximately 2-3 cm.

Magnetic resonance imaging was carried out on a Picker Corp. Whole Body Superconducting System operating at 0.3 T using a 30 cm transmitter coil tuned to 0.26 T (10.08 MHz). Maximum contrast of the colon carcinoma implants was obtained with a spin echo image sequence (TE-26 msec, TR-250 msec) and with an inversion recovery image sequence (TI-400-600 msec, TR-1500 msec). The mice were sedated with prior injection of pentobarbital, and the metalloporphyrins were injected intravenously into the tail.

The Mn(III) complexes with tetra-N-methyl-4-pyridyl) porphyrin (TMPyP; slope - 7.50±0.03 (mM sec)$^{-1}$) and with tetra(N-trimethylanilinium) porphyrin (TAP; 9.35±0.03 (mM sec)$^{-1}$) were comparable to the value for Mn(III) tetra phenyl sulfonyl porphyrin (TPPS4; 10.36±0.09 (mM sec)$^{-1}$). The homologous Fe(III) complexes gave slopes approximately half these values. Tissue $T_1$ analysis of the tumor before and after infusion of Mn(III)TMPyP gave a 50% decrease in the measured $T_1$ value. Consequently, the Mn(III) complexes were chosen for MRI testing using the athymic mice-colon cancer system. Preliminary results with Mn(III)TMPyP and then TPPS4 showed a significant enhancement in contrast for the colon tumor relative to the rest of the tissue. A clear demonstration of this effect was obtained by imaging two mice, one control untreated, and one treated side-by-side.

EXPERIMENT 3

Figure 2:
FIG. 2 is a photograph from an NMR image of 3 mice, right untreated, middle treated with 4 mg Mn(III)TPPS$_4$, left with 6 mg Mn(III)TPPS$_4$.

These compounds were then tested using a Picker Corp. whole body imager in the Diagnostic Radiology Dept. at NIH. This operates at 0.26T, and a 30 cm coil was used which gave sufficient resolution to image a mouse. The MnTPPS4 and several other Mn(III) complexes (TMPyP, TAP) were injected in aqueous solution at a pH adjusted to around neutrality (4–6 mg in 0.1 ml) intraveneously into the tail of nude mice with large (2–3 cm) implanted human colon carcinoma. Both spin echo ($T_2$) and inversion recovery $T_1$) images showed enhancement of contrast in the treated animals (see FIG. 2). Images were taken after 10 min., 30 min., 1 hr., 24 hrs., and 48 hrs. In the later times the contrast was improved (all images were directly compared with an untreated mouse). Tissue relaxation times of bulk water of animals sacrificed after imaging showed significant changes in relaxation times (e.g., ca. 50% for the tumor of treated vs. untreated animals).

The foregoing description of the specific embodiments will so fully reveal the general nature of the invention that others can, by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is to be understood that the phrasiology or terminology employed herein is for the purpose of description and not of limitation.

What is claimed is:

1. A method of enhancing an image obtained from magnetic resonance imaging of a region containing a malignant tumorous growth comprising the steps of administering to a subject a non-lethal amount of a water-soluble paramagnetic Mn(III) porphyrin, or a pharmaceutically acceptable acid form or salt thereof effective to significantly enhance the contrast in a magnetic resonance image between said malignant tumorous growth and the remainder of said image; and then
   imaging said region of said subject by magnetic resonance.

2. The method of claim 1 wherein the porphyrin portion of said metalloporphyrin is tetrasulfonated tetraphenylsulfonyl porphyrin, tetra(N-methyl-4-pyridyl) porphyrin, methylated tetrasulfonated tetraphenylsulfonyl porphyrin or tetra (N-methylanilinium) porphyrin and pharmaceutically acceptable acid forms and salts thereof effective to significantly enhance the contrast in a magnetic resonance image between said malignant tumorous growth and the remainder of said image; and then
   imaging said region of said subject by magnetic resonance.

3. The method of claim 2, wherein said metalloporphyrin is administered intervenously or by infusion.

4. The method of claim 3, wherein the porphyrin portion of said metalloporphyrin is tetrasulfonated tetraphenylsulfonyl porphyrin.

* * * * *